United States Patent [19]

Swank

[11] 4,116,845

[45] Sep. 26, 1978

[54] HIGH CAPACITY BLOOD TRANSFUSION MICRO FILTER

[75] Inventor: Roy L. Swank, Portland, Oreg.

[73] Assignee: Pioneer Filters, Inc., Beaverton, Oreg.

[21] Appl. No.: 820,791

[22] Filed: Aug. 1, 1977

Related U.S. Application Data

[63] Continuation-in-part of Ser. No. 807,378, Jun. 17, 1977.

[51] Int. Cl.[2] ............ B01D 27/00

[52] U.S. Cl. ............ 210/446; 210/451; 210/455; 210/DIG. 23

[58] Field of Search ............ 210/435, 445, 446, 451, 210/455, DIG. 23

[56] References Cited

U.S. PATENT DOCUMENTS

| | | | |
|---|---|---|---|
| 3,448,041 | 6/1969 | Swank | 210/446 X |
| 3,462,361 | 8/1969 | Greenwalt et al. | 210/446 X |
| 3,593,854 | 7/1971 | Swank | 210/446 X |
| 3,935,111 | 1/1976 | Bentley | 210/446 |

*Primary Examiner*—Thomas G. Wyse
*Assistant Examiner*—Richard W. Burks
*Attorney, Agent, or Firm*—Eugene D. Farley

[57] ABSTRACT

A high capacity blood transfusion micro filter comprises a case having inlet and outlet ports, upper and lower chambers, inward projections in the upper chamber and a quantity of woolly blood filter material contained in both chambers. The woolly material in the upper chamber is of less density than that in the lower chamber and is fluffed out into the spaces between the projections to provide filter areas of still lower density. Baffle means direct the flow of blood centrally in both upper and lower chambers.

9 Claims, 5 Drawing Figures

HIGH CAPACITY BLOOD TRANSFUSION MICRO FILTER

This application is a continuation-in-part of the patent application of Roy L. Swank Ser. No. 807,378, filed June 17, 1977, for BLOOD FILTERING APPARATUS OF GRADUATED FIBER DENSITY.

BACKGROUND AND GENERAL STATEMENT OF THE INVENTION

This invention pertains to blood filters. It relates particularly to continuous high volume blood filtering devices of the class employed principally in making blood transfusions.

It presently is routine medical practice when making blood transfusions to employ blood bank blood. As is well known, this is prepared by withdrawing blood from donors, adding heparin and other preservatives, and then storing the blood under carefully controlled conditions until its use is required.

In the use of the blood, there have been observed in the patient complications, sometimes serious, which have been recognized as being a function of blood storage duration. Accordingly, it has been common practice to discard blood bank blood after it has been stored for a predetermined time.

It has been discovered that when blood bank blood is stored, its leukocyte and platelet components are altered, developing characteristics which are responsible for the transfusion complications referred to above. The alteration is evidenced in two ways.

First, some of the platelets become adhesive. Second, some of the platelets form aggregates with some of the leukocytes. The aggregates primarily are responsible for the adverse results occurring when old blood is used in blood transfusions. In addition, when carrying out auto transfusions, the blood becomes contaminated with extraneous material such as epithelium, pieces of muscle, fat emboli, fragments of suture material and the like.

The importance of removing foreign material such as the above from the blood before introducing it into the patient is obvious.

My U.S. Pat. No. 3,593,854 describes and illustrates a blood treating and filtering apparatus overcoming the foregoing problem which has been used widely and successfully. However, continued surgical experience with the unit has shown that the fibrous filter mat used in it tends to become clogged at its upstream, or presenting surface before the filtering capacity of the filter is reached. This materially shortens the life of the filter and adds expense and inconvenience to the blood filtering operation.

The causes of clogging of the filter are two-fold; First, the comparatively high density of the filter material at the presenting surface provides relatively small filter surface openings which rapidly become plugged with debris. Second, the construction of the filter is such that a relatively small filter surface area is presented to the incoming blood.

The first of the foregoing disadvantages has been overcome in my co-pending application Ser. No. 807,378 of which the present application is a continuation-in-part. This application describes and illustrates a blood filter having a filamentous or fibrous filtering component arranged within the filter in such a manner that the filter body is of graduated density i.e. has a lesser density at its presenting surface than it does at its exit surface with the density progressively increasing throughout the body of the filter. As a result of this arrangement, the presenting surface of the filter filters out the larger particles while the exiting surface filters out the minute particles, thereby putting to work the entire body of the filter, rather than just the presenting surface portion thereof.

The filter of my patent application Ser. No. 807,378 aforesaid is, however, particularly suited for application in the technique of open heart surgery and related operations and is not so well suited for use in blood transfusions.

It accordingly is the general purpose of the present invention to provide a high capacity, rapid, blood filter for use in making blood transfusions and auto transfusions.

It is another principal object of the present invention to provide a blood transfusion micro filter of comparatively small size which retains a relatively small amount of the blood being transfused, with the consequent advantage to the patient.

Still another object of the present invention is the provision of a blood transfusion micro filter characterized by rapid flow.

A further object of the present invention is the provision of a transfusion type micro filter simple in construction, low in cost, efficient in operation (with particular regard to freedom from channeling) and well adapted for use in present day operating procedures without extensive modification thereof.

Generally stated, the high capacity blood transfusion micro filter of my invention broadly comprises a substantially vertically arranged case terminating at its upper and lower ends in inlet and outlet ports, respectively. A plurality of radially spaced ribs or other projections extend inwardly from the inner surface of the upper portion of the case. Perforate blood filter material support means is positioned across the lower portion of the case a spaced distance below the projections to form a chamber. A quantity of woolly or filamentous blood filter material is contained in the chamber, fluffed into the spaces between the projections to provide filter areas of decreased filter material density.

Preferably, the case is divided into two chambers: An upper chamber containing filter material of decreased density and a lower chamber containing filter material of relatively greater density.

Combination baffle means and filter material densifying means is provided in the interior of the case for directing the flow of blood inwardly through the filter material.

DETAILED DESCRIPTION OF A PREFERRED EMBODIMENT OF THE INVENTION

Figures 1, 2, 3, 4, 5:
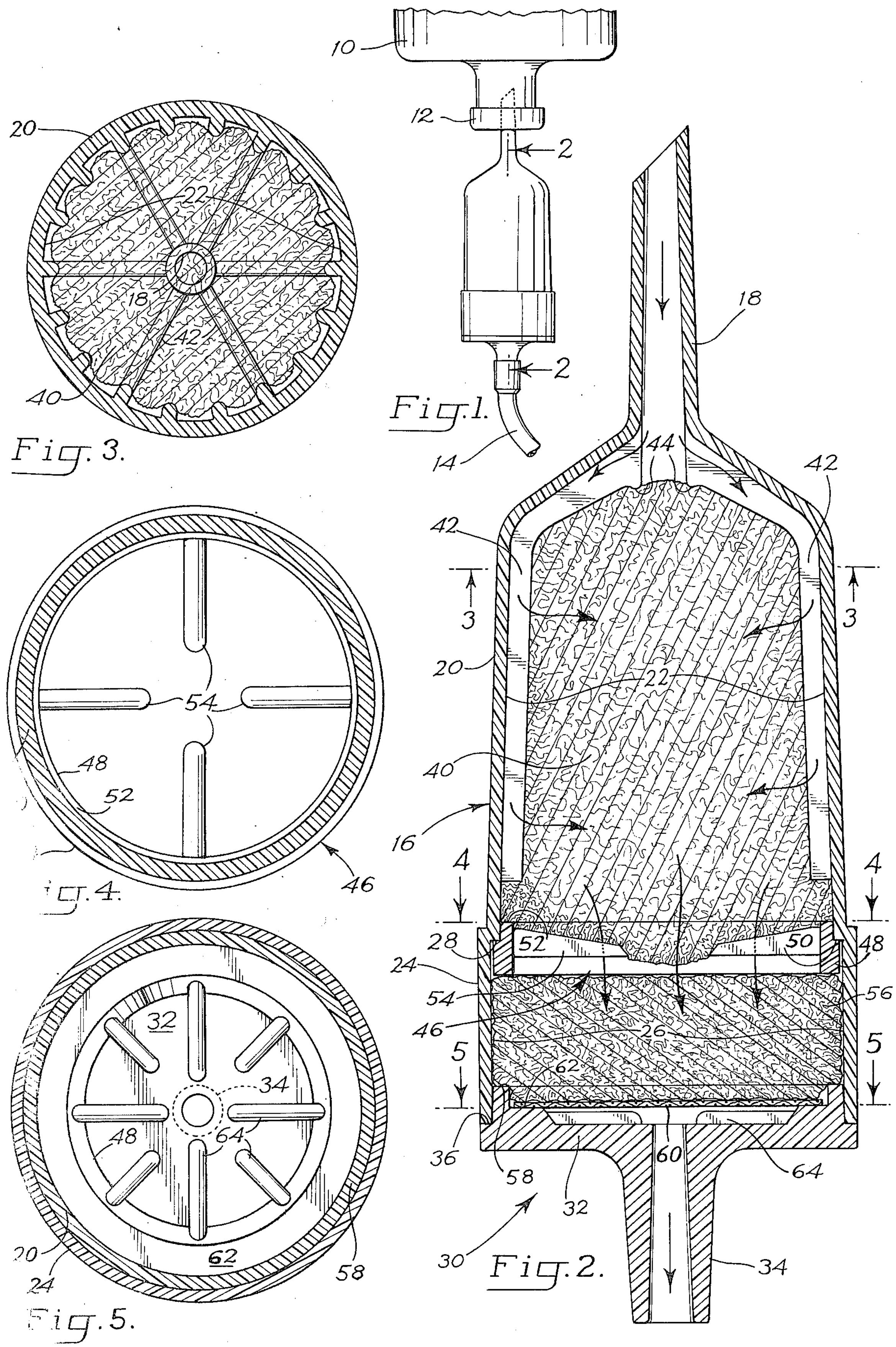

The high capacity blood transfusion micro filter of my invention is described herein with reference to the drawings wherein:

FIG. 1 is a view in side elevation of the filter in the operative position in which it is used in filtering blood during blood transfusions.

FIG. 2 is an enlarged longitudinal section taken along line 2—2 of FIG. 1 and FIGS. 3, 4 and 5 are transverse sectional views taken along lines 3, 4 and 5 respectively of FIG. 2.

Referring to FIGS. 1 and 2:

FIG. 1 illustrates the filter in its application to the transfer of blood from a receptacle to the circulatory system of a patient. When transfusing blood bank blood, the receptacle 10 comprises the vessel in which the blood is stored. In the case of an auto transfusion, receptacle 10 represents a reservoir in which the patient's own blood is collected during an operative procedure. In either case the receptacle is equipped with a closure 12 comprising a rubber or plastic diaphragm penetratable by a spur-type puncturing implement.

The filter of the invention is positioned immediately below the receptacle 10, with which it communicates, for gravitational or pumped flow of the blood. At its lower end, the filter communicates with a tube 14 which conveys the blood to the circulatory system of the patient.

The filter is housed in a case indicated generally at 16 adapted to be arranged vertically and terminating at its upper and lower ends in inlet and outlet ports respectively. Preferably, case 16 is formed in segments from a single piece of molded plastic.

At its upper end, case 16 is formed with a penetrating spur 18 which is hollow and provides the inlet port for the case. It is adapted to penetrate the cap 12 of blood storage receptacle 10 in the manner illustrated in FIG. 1.

Immediately below spur 18 is a case segment 20 of enlarged cross section which defines a first or upper filter chamber 22.

Immediately below filter chamber 22 is a case segment 24 of still greater cross section which defines a second or lower filter chamber 26.

It is to be noted that by offsetting case segment 26 from case segment 30 there is formed an inner annular shoulder 28.

In the preferred embodiment, the bottom of case 16 is open and fitted with a cap piece indicated generally at 30. This piece also is made of molded plastic. It comprises a body part 32 and a tubular extension 34 which communicates with the interior of the case and provides the downstream outlet port therefrom.

Cap piece 30 is connected in sealed relation to case 16 by the provision of an upper part of reduced cross section which fits within the case and is provided with a shoulder 36 against which the edge of case 16 seats.

Upper chamber 22 is filled with a loose packing of filter material in the form of a filamentous wool 40. As set forth in my abovementioned U.S. Pat. No. 3,593,854, woolly materials suitable for this purpose are fibrous or filamentous polyester resin (Dacron and Kodel), fibrous polyamide resin (Nylon), filamentous polyacrylic resin (Orlon), glass wool, steel wool, cotton, and cellulose (paper). The wool is arranged in upper chamber 22 in a manner such as to present to the incoming blood a large filtering surface of decreased density.

To this end, the inner side wall of chamber 22 is provided with a plurality of inwardly extending projections. In the preferred form of the invention, these projections comprise radially spaced, inwardly projecting ribs 42. The ribs are formed integrally with the case and terminate at their upper ends in small hook-like projections 44 which have as their function retaining the wool within the chamber. In effect, they replace screen 34 of the form of the invention shown in FIG. 1 of my aforesaid U.S. Pat. No. 3,593,854. This simplifies the construction of the apparatus and, more importantly, increases the rate of flow while at the same time increasing materially the service life of the unit.

Ribs 42 terminate a spaced distance upwardly from the lower margin of reduced segment 30 of case 16. This is of material importance in determining the efficient operation of the filter.

When chamber 22 is packed with the filter wool, the wool fills the entire chamber and loops into the recesses between ribs 42 in the manner shown in FIG. 3. As a result, there are provided channels along the side wall of the chamber through which the blood flows quickly. It also provides fluffed areas of woolly material on the presenting surface of the filter which are easily penetrated by the blood since they act only to filter out the largest of its content of entrained solid particles.

Filter material 40 is retained in upper chamber 22 by means of a perforate support indicated generally at 46. This support serves the triple purposes of supporting the filter material in the chamber, of passing the filtered blood into the chamber below, and of diverting the flow of blood toward the center of the chamber for more efficient filtration.

The manner in which the latter function is achieved will be apparent particularly from an inspection of FIG. 2.

Support 46 broadly comprises an annular body 48 having an external annular shoulder 50 which engages internal shoulder 28 of the case and positions the support properly within the case.

Extending upwardly from the body 48 of the support is a flange 52 which seats within upper chamber 22 in tightly sealing engagement therewith. This flange also operates as a piston when the support is located, since as it enters the upper chamber it compresses appreciably the packing material located along the inside margin of the upper chamber below the lower ends of ribs 42 which, it will be recalled, terminate short of case segment 20 in order to achieve this purpose. These two factors, i.e. the baffle effect of the upper surface of flange 52 and the densification of the fibrous filter material along the inner lower side wall of chamber 22, cause the blood to flow inwardly toward the center of the filter, an effect which is promoted further by the provision of radial vanes or guides 54 mounted upon and extending inwardly from the inner surface of support 46.

Located within lower chamber 26, below support 46 by which it is partly restrained, is a second quantity of filter material 56.

This filter material is of the same general character as filter material 40 in the upper chamber. It accordingly comprises filamentous woolly material capable of removing the foreign solid particles from the blood. However, it is packed more densely with the object in view of removing from the blood the minute particles not removed by packing 40 in the upper chamber.

Although the relative densities of the two filter packings may be varied to suit particular applications, I have found a preferred ratio to be provided when the upper filter packing has a density of from 12 to 22 ccs. per gram and the lower packing has a density of from 6 to 8 ccs. per gram.

As in the case of the upper chamber, means are provided in the lower chamber for insuring that the blood will pass inwardly to the center of the packing rather than channeling along the outside edges thereof.

For this purpose, cap piece 30 is provided with an upwardly extending annular flange 58. This flange serves the same functions as does flange 52. It fits snugly within the bore of case segment 24, sealing the chamber. It serves as a baffle which directs the downwardly flowing blood inwardly into the packing. It also has a piston effect, compressing and densifying the packing around its margins so that the blood flow further is encouraged to proceed toward the interior of the filter.

To provide a means for removing any particles or fragments of the filter material which might inadvertently have become entrained in the blood, there is provided a screen 60 which may be made of Nylon or other material not degrading to the blood nor injurious to the patient. The screen is seated against and glued to an annular land 62 with which the interior of cap 30 is provided.

Blood passing through the screen flows onto the floor of the cap piece, where it is directed by vanes 64 to outlet 34.

OPERATION

The manner of operation of the blood transfusion micro filter of my invention is as follows:

With cap piece 30 removed, upper chamber 22 is filled with woolly filamentous packing which is prevented from too extensively entering outlet 18 by hooks 44 on ribs 42. As seen in FIG. 3, the packing is loosely fluffed between ribs 42 so that the presenting surface of the filter material is of lowest density, retaining only the largest foreign particles.

Support 46 next is put in place. As this is done, marginal flange 52 compresses appreciably the woolly filter material along the lower margin of upper chamber 22, below ribs 42, to provide an area of increased density.

Packing 56 having a density greater by predetermined degree than the density of packing 40 in the upper chamber then is inserted in lower chamber 26. Cap piece 30 is placed across the open lower end of case 16. It is maintained permanently in this position by application of a suitable adhesive to the meeting surfaces. Support 46 on the other hand is maintained in position frictionally and by the pressure support of packing 56 in the lower chamber.

As cap piece 30 is put in position, the same effect occurs as when support 46 is put in position. Flange 58 compresses the marginal filter material at the bottom of the chamber, appreciably increasing its density.

When the assembled filter is put in use, as illustrated in FIG. 1, the blood enters through inlet 18. At first, the blood flows rapidly along the periphery of chamber 22 until it encounters the resistance afforded by flange 52 and the compressed packing immediately upstream from the flange. Because of this resistance, a column of blood is formed which almost completely fills the filter. The blood in chamber 22 then filters inwardly and downwardly in the direction of the arrows of FIG. 2. As it does so, it filters through areas of differential density. First it flows through the loosely fluffed filter material between ribs 42 and thereafter through the more densely packed material in the interior of the filter.

After the blood has left the chamber 22, it gravitates into lower chamber 26, containing more densely packed wool, where the same effect occurs: it first passes centrally through the wool as indicated by the arrows. Any blood passing along the side walls meets the densified lower portion of the packing, whereupon it is directed inwardly through the filter. Since the main body of filter material 56 is substantially more dense than is the filter material contained in the upper chamber, it acts to screen out the smallest of the foreign particles it is desired to remove.

After passing through filter material 56, the blood passes through screen 60 which removes any fragments of filter material which the blood may have entrained. Thereafter it exits from the filter through outlet 34.

By reason of the efficient operation of the filter, and in particular by reason of the fact that the filter surface is enlarged to encompass substantially the entire inner surface of case 16, while at the same time utilizing the principle of selective filtration, i.e. removing the particles in size order, the filter of the invention becomes in fact a micro filter in that its size is only a fraction of the size of the prior art filters. A filter of commercial size of about 1½ inches in diameter by 3 inches in length is completely adequate for use in filtering transfusion blood. This result is achieved while achieving the other significant advantages of increasing the capacity of the filter by from 50 to 150% and materially decreasing the hold-up of blood in the filter.

Having thus described by invention in preferred embodiments, I claim:

1. A blood transfusion micro filter comprising:

(a) a substantially vertically arranged elongated case having a peripheral wall terminating at its upper and lower ends in walls provided with inlet and outlet ports, respectively, (b) a plurality of peripherally spaced longitudinal projections extending inwardly from the inner surface of the upper end wall and from the upper portion of the peripheral wall of the case, (c) perforate blood filter material support means traversing the peripheral wall a spaced distance below the projections to form a chamber thereabove, and (d) a quantity of woolly blood filter material contained in the chamber and fluffed into the spaces between the peripherally spaced projections to provide therein filter areas of decreased filter material density.

2. The micro filter of claim 1 wherein the case is circular in cross section and the projections comprise radially extending, circumferentially spaced ribs.

3. The micro filter of claim 1 wherein the projections comprise spaced ribs, the upper ends of which terminate adjacent the inlet port and are provided with downwardly directed hook-like projections arranged for engageing and retaining in the chamber the upper portion of the filter material.

4. The micro filter of claim 1 wherein the perforate blood filter material support means includes inwardly extending baffle means arranged to provide decreasing densification of the filter material inwardly toward the center of the case for directing the flow of blood centrally through the filter material.

5. The micro filter of claim 1 wherein the case includes a lower portion of increased diameter connected to the upper portion through an annular shoulder, and wherein the blood filter support means has an exterior annular shoulder dimensioned for nesting engagement with the annular shoulder of the case, and peripherally spaced vanes extending inwardly from the annular shoulder, the upper sides of the vanes sloping downward toward the center, thereby forming an inwardly projecting baffle directing the flow of blood centrally through the filter material.

6. The micro filter of claim 1 wherein the case is extended downwardly from the support means to form a second chamber and in the second chamber a second quantity of woolly blood filter material packed to a density substantially greater than the density of the filter material in the first named chamber.

7. The micro filter of claim 6 wherein the filter material in the first chamber has a density of 1 gram for from 12 to 22 cubic centimeters and the filter material in the second chamber has a density of 1 gram for from 6 to 8 cubic centimeters.

8. The micro filter of claim 1 wherein the bottom of the case is open and including a bottom cap piece sealed across the open lower end of the case and formed with a central outlet port, the cap piece providing an interior baffle arranged to provide decreasing densification of the filter material inwardly toward the center of the case for directing the flow of blood inwardly through the filter material.

9. A high capacity blood transfusion micro filter comprising:

(a) a substantially vertically arranged elongated case having a peripheral wall terminating at its upper end in a wall provided with an inlet port and open at its lower end, (b) a plurality of peripherally spaced longitudinal ribs extending inwardly from the inner surface of the upper end wall and from the upper portion of the peripheral wall of the case and terminating at their upper ends in downwardly extending hooks, (c) perforate blood filter material support means traversing the peripheral wall of the case a spaced distance below the ribs to form a first chamber thereabove, (d) the blood filter support means being formed with an integral inwardly extending baffle arranged to provide decreasing densification of the filter material inwardly toward the center of the case for directing the flow of blood centrally of the case, (e) a first quantity of woolly blood filler material contained in the first chamber and fluffed out into the spaces between the peripherally spaced ribs to provide therein filter areas of decreased filter density, (f) a cap piece fitted across the open lower end of the case and provided with an outlet port, thereby forming a second chamber below the support means, (g) a second quantity of woolly blood filter material contained in the second chamber, (h) the filter material in the second chamber having a substantially higher density than the filter material in the first chamber, (i) and an inwardly projecting peripheral baffle carried by the cap piece arranged to provide decreasing densification of the filter material inwardly toward the center of the case for directing the flow of blood centrally of the case toward the outlet port.

* * * * *